United States Patent
Deligianni et al.

(10) Patent No.: US 12,023,162 B2
(45) Date of Patent: Jul. 2, 2024

(54) THREE-DIMENSIONAL SILICON-BASED COMB PROBE WITH OPTIMIZED BIOCOMPATIBLE DIMENSIONS FOR NEURAL SENSING AND STIMULATION

(71) Applicants: International Business Machines Corporation, Armonk, NY (US); Yale University, New Haven, CT (US)

(72) Inventors: Hariklia Deligianni, Alpine, NJ (US); Jason Gerrard, Madison, CT (US); Emily R. Kinser, Poughkeepsie, NY (US); Themis R. Kyriakides, Branford, CT (US); Dennis D. Spencer, Woodbridge, CT (US); Roy R. Yu, Poughkeepsie, NY (US); Hitten Zaveri, New Haven, CT (US)

(73) Assignees: International Business Machines Corporation, Armonk, NY (US); Yale University, New Haven, CT (US)

( * ) Notice: Subject to any disclaimer, the term of this patent is extended or adjusted under 35 U.S.C. 154(b) by 796 days.

(21) Appl. No.: 16/204,607

(22) Filed: Nov. 29, 2018

(65) Prior Publication Data
US 2020/0170523 A1 Jun. 4, 2020

(51) Int. Cl.
*A61B 5/00* (2006.01)
*A61B 5/24* (2021.01)
(Continued)

(52) U.S. Cl.
CPC .............. *A61B 5/24* (2021.01); *A61B 5/685* (2013.01); *A61N 1/0531* (2013.01);
(Continued)

(58) Field of Classification Search
CPC ..... A61B 5/24; A61B 5/291; A61B 2562/046; A61B 2562/125; A61B 5/369;
(Continued)

(56) References Cited

U.S. PATENT DOCUMENTS

| 4,969,468 A | 11/1990 | Byers et al. |
| 6,171,239 B1 * | 1/2001 | Humphrey ............. A61B 5/375 600/372 |

(Continued)

FOREIGN PATENT DOCUMENTS

| CN | 104502429 A | 10/2015 |
| CN | 107589163 A | 1/2018 |

(Continued)

OTHER PUBLICATIONS

Cristina Camagong et al., "Nanostructure Featuring Nano-Topography With Optimized Electrical and Biochemical Properties", U.S. Appl. No. 16/204,545, filed Nov. 29, 2018.

(Continued)

*Primary Examiner* — Joseph A Stoklosa
*Assistant Examiner* — Brian M Antiskay
(74) *Attorney, Agent, or Firm* — CANTOR COLBURN LLP; Stosch Sabo

(57) ABSTRACT

A structure for monitoring and stimulation includes an external power supply unit. The structure also includes an internal hub communicatively coupled to the external power supply unit. The structure further includes a plurality of sensor modules communicatively coupled to the internal hub by a plurality of flexible interconnects. The plurality of sensor modules include three-dimensional (3D) comb sensor devices.

14 Claims, 5 Drawing Sheets

(51) Int. Cl.
*A61N 1/05* (2006.01)
*A61N 1/36* (2006.01)

(52) U.S. Cl.
CPC .. *A61N 1/36135* (2013.01); *A61B 2560/0214* (2013.01); *A61B 2562/0209* (2013.01); *A61B 2562/028* (2013.01); *A61B 2562/0285* (2013.01); *A61B 2562/046* (2013.01); *A61B 2562/125* (2013.01)

(58) Field of Classification Search
CPC ..... A61B 5/685; A61B 5/6814; A61B 5/6868; A61B 2562/028; A61B 5/0031; A61B 2018/00434; A61B 2018/0044; A61B 2560/0219; A61B 2562/0285; A61B 5/0006; A61B 5/686; A61B 5/25; A61N 1/0534; A61N 1/0551; A61N 1/0529
USPC ................ 600/372, 373, 377–378, 544–545; 607/115–118, 120
See application file for complete search history.

(56) References Cited

U.S. PATENT DOCUMENTS

| | | | |
|---|---|---|---|
| 6,359,444 | B1 | 3/2002 | Grimes |
| D469,540 | S | 1/2003 | Holker et al. |
| 6,914,279 | B2 | 7/2005 | Yichenglu et al. |
| 7,005,048 | B1 | 2/2006 | Watanabe et al. |
| 7,006,859 | B1* | 2/2006 | Osorio ................. A61N 1/0539 600/378 |
| 7,212,851 | B2 | 5/2007 | Donoghue et al. |
| 7,294,910 | B2 | 11/2007 | Thomas et al. |
| 7,524,408 | B2 | 4/2009 | Monbouquette et al. |
| 7,894,914 | B2 | 2/2011 | Stahmann et al. |
| 7,946,050 | B2* | 5/2011 | Chiou ................ G01R 1/07321 33/557 |
| 7,949,382 | B2 | 5/2011 | Jina |
| 7,955,483 | B2 | 6/2011 | Gu et al. |
| 8,076,125 | B2 | 12/2011 | Mcgimpsey |
| 8,097,926 | B2 | 1/2012 | De Graff et al. |
| 8,221,822 | B2 | 7/2012 | Flanagan et al. |
| 8,255,061 | B2* | 8/2012 | Perlin .................... A61B 5/685 607/116 |
| 8,355,768 | B2* | 1/2013 | Masmanidis ........ A61B 5/4041 600/378 |
| 8,529,835 | B2 | 9/2013 | Kaplan et al. |
| 8,574,789 | B1 | 11/2013 | Shelnutt et al. |
| 8,668,978 | B2 | 3/2014 | Malima et al. |
| 8,708,966 | B2 | 4/2014 | Allen et al. |
| 8,741,380 | B2 | 6/2014 | Yoshida et al. |
| 8,772,228 | B2 | 7/2014 | Stupp et al. |
| 8,808,516 | B2 | 8/2014 | Melosh et al. |
| 8,831,750 | B2 | 9/2014 | Ramachandran et al. |
| 8,888,969 | B2 | 11/2014 | Soleymani et al. |
| 9,095,267 | B2 | 8/2015 | Halpern et al. |
| 9,243,277 | B2 | 1/2016 | Rajagopal et al. |
| 9,399,128 | B2* | 7/2016 | Tooker ..................... A61B 5/24 |
| 9,662,498 | B1 | 5/2017 | Son et al. |
| 9,844,660 | B2 | 12/2017 | Vetter et al. |
| 2003/0100823 | A1* | 5/2003 | Kipke .................. A61B 5/4041 607/116 |
| 2005/0269285 | A1 | 12/2005 | Jung et al. |
| 2006/0293578 | A1 | 12/2006 | Rennaker, II |
| 2007/0106143 | A1* | 5/2007 | Flaherty ............... A61N 1/0531 600/373 |
| 2008/0177363 | A1* | 7/2008 | Schouenborg ....... A61N 1/0551 607/116 |
| 2008/0214920 | A1 | 9/2008 | Merz et al. |
| 2009/0155800 | A1 | 6/2009 | Hong et al. |
| 2009/0243584 | A1 | 10/2009 | Zhang et al. |
| 2010/0006451 | A1 | 1/2010 | Gordon et al. |
| 2010/0066346 | A1 | 3/2010 | Zhang et al. |
| 2010/0241086 | A1 | 9/2010 | Yodfat et al. |
| 2010/0318193 | A1 | 12/2010 | Desai et al. |
| 2011/0091510 | A1 | 4/2011 | Lele et al. |
| 2011/0230735 | A1 | 9/2011 | Wolfe et al. |
| 2011/0301716 | A1 | 12/2011 | Sirinrathsirivisoot et al. |
| 2012/0218550 | A1 | 8/2012 | O'Mahony |
| 2013/0200437 | A1 | 8/2013 | Rha |
| 2014/0230354 | A1 | 8/2014 | Lopez et al. |
| 2014/0238574 | A1 | 8/2014 | Kinser et al. |
| 2015/0133761 | A1* | 5/2015 | Vetter ...................... A61B 5/24 600/378 |
| 2016/0041159 | A1 | 2/2016 | Labaer et al. |
| 2016/0257959 | A1 | 9/2016 | Alsager et al. |
| 2016/0281147 | A1 | 9/2016 | Besant et al. |
| 2017/0007813 | A1* | 1/2017 | Negi ................... A61B 5/6868 |
| 2017/0209079 | A1 | 7/2017 | Kinser et al. |
| 2018/0020957 | A1 | 1/2018 | Kinser |
| 2018/0353750 | A1* | 12/2018 | Hetke .................. A61B 5/287 |
| 2020/0173953 | A1 | 6/2020 | Camagong et al. |
| 2020/0176262 | A1 | 6/2020 | Camagong et al. |

FOREIGN PATENT DOCUMENTS

| | | |
|---|---|---|
| KR | 101203898 B1 | 11/2012 |
| WO | 2010003212 A1 | 1/2010 |

OTHER PUBLICATIONS

Cristina Camagong, et al., "Nanostructure Featuring Nano-Topography With Optimized Electrical & Biochemical Properties", U.S. Appl. No. 16/204,438, filed Nov. 29, 2018.

Deshpande et al., "Development of a nanoscale heterostructured glucose sensor using modified micorfabrication processes", J. of Micro/Nanolithography MEMS MEOMS, vol. 7(2), Apr.-Jun. 2008, 6 pages.

Freckmann et al. "System Accuracy Evaluation of 27 Blood Glucose Monitoring Systems According to DIN EN ISO 15197", Diabetes Technology & Therapeutics, vol. 12, No. 3, 2010, 12, pp. 221-231.

Janine Gajdzik, et al., "Enzyme immobilisation on self-organised nanopatterned electrode surfaces", www.rsc.org/pccp | Physical Chemistry Chemical Physics, Received Jun. 16, 2010, Accepted Aug. 12, 2010, pp. 12604-12607.

List of IBM Patents or Patent Applications Treated as Related; (Appendix P), Filed Nov. 30, 2018, 2 pages.

Marco Cardosi et al., "Amperometric Glucose Sensors for Whole Blood Measurement Based on Dehydrogenase Enzymes", Intech Open Science Open Minds, Chapter 13, 2012 pp. 319-354.

Parng, et al., "Effect of temperature and glucose concentration on a glass-based sensor for long-term stability investigation", Journal of Micro/Nanolithography MEMS MEOMS. vol. 10(1) Jan.-Mar. 2011 pp. 5.

Roy R. Yu, et al., "Three-Dimensional Silicon-Based Comb Probe", U.S. Appl. No. 16/204,703, filed Nov. 29, 2018.

S. Martel et al., "Development of a wireless brain implant: the telemetric electrode array system (TEAS) project." 23rd Annual International Conference of the Engineering in Medicine and Biology Society, 2001, pp. 3594-3597.

Sohee Kim et al., "Thermal impact of an active 3-D microelectrode array implanted in the brain." IEEE Transactions on Neural Systems and Rehabilitation Engineering, vol. 15, No. 4, 2007, pp. 493-501.

Zhai et al., "Highly Sensitive Glucose Sensor Based on Pt Nanoparticle/Polyaniline Hydrogel Heterostructures", ACS Nanoparticles, vol. 7(4), 2013, pp. 3540-3546.

Kinser, Emily R. et al., "Nanopatterned Bulk Metallic Glass Biosensors", ACS Sensors, vol. 2, No. 12, 2017, 30 pp.

Padmanabhan et al., "Engineering Cellular Response Using Nanopatterned Bulk Metallic Glass", ACS Nano Article, 2014, vol. 8, No. 5, pp. 4366-4375.

Yuan Yuan et al., "Seed-mediated synthesis of dendritic platinum nanostructures with high catalytic activity for aqueous-phase hydrogenation of acetophenone", Journal of Energy Chemistry 24 (2015) 660-668.

Cao et al., "Template-based synthesis of nanorod, nanowire, and nanotube arrays", Advances in Colloid and Interface Science 2008, 136, pp. 45-64. Available online Jul. 26, 2007 (Year: 2007).

(56) References Cited

OTHER PUBLICATIONS

Lou et al., "Electroplating", Encyclopedia of Chemical Processing, 2006 (10 pages).
Zou et al., "Dendritic Heterojunction Nanowire Arrays for High-Performance Supercapacitors", Scientific Reports 5:7862 (Year: 2015) 7 pages.

* cited by examiner

THREE-DIMENSIONAL SILICON-BASED COMB PROBE WITH OPTIMIZED BIOCOMPATIBLE DIMENSIONS FOR NEURAL SENSING AND STIMULATION

BACKGROUND

The present invention generally relates to neural sensing and stimulation. More specifically, the present invention relates to three-dimensional (3D) silicon-based comb probes with optimized biocompatible dimensions for neural sensing and stimulation.

A brain machine interface (BMI) is a device that translates neuronal information into commands capable of controlling external software or hardware, such as a computer or robotic arm. BMIs can be used as, for example, assisted living devices for individuals with motor or sensory impairments. BMIs therefore hold great promise for restoration of function in persons with neurological deficits.

The field of BMI research and development has focused on neuro-prosthetic applications that aim at restoring damaged hearing, sight, and movement. Due to the remarkable cortical plasticity of the brain, signals from implanted prostheses can, after adaptation, be handled by the brain like natural sensor or effector channels.

Recent work has involved the development of intra-cortical microelectrode arrays for brain-machine interfacing processes that attempt to interrogate the complex neural networks of the brain. For example, some brain implants used to monitor electrical signals include two-dimensional (2D) grids of macroscale electrodes that are arranged on a top surface of the brain. In other examples, brain probes include macroscale electrodes that are inserted deep into the brain. In addition to sensing of neural activity for monitoring purposes, in vivo brain probes also can be utilized to transmit electrical signals in order to modulate brain activity, as is often the case with devices inserted deep into the brain.

SUMMARY

Embodiments of the present invention are directed to a structure for monitoring and stimulation. A non-limiting example of the structure includes an external power supply unit. The structure also includes an internal hub communicatively coupled to the external power supply unit. The structure further includes a plurality of sensor modules communicatively coupled to the internal hub by a plurality of flexible interconnects. The plurality of sensor modules include three-dimensional (3D) comb sensor devices.

Embodiments of the present invention are directed to a three-dimensional (3D) comb sensor structure. A non-limiting example of the structure includes a plurality of sensor modules. Each sensor module of the plurality includes a two-dimensional (2D) micro-grid array including a plurality of first sensing elements, a first comb, and a second comb. Each of the first comb and second comb is communicatively coupled to the 2D micro-grid array and includes a plurality of second sensing elements. Each sensor module of the plurality further includes a logic chip coupled to the 2D micro-grid array that controls power distribution and data interface between the 2D micro-grid array and each of the first comb and the second comb.

Another non-limiting example of the three-dimensional (3D) comb sensor structure includes a first comb and a second comb. Each of the first comb and the second comb is coupled to a two-dimensional (2D) micro-grid array and includes sensing elements containing a plurality of nan- orods. The 3D comb sensor structure further includes a logic chip coupled to the 2D micro-grid array that controls power distribution and data interface between the 2D micro-grid array and each of the first comb and the second comb.

Embodiments of the present invention are directed to a method of forming a neural three-dimensional (3D) sensor comb structure. A non-limiting example of the method includes fabricating a comb structure including a plurality of shanks including sensing elements containing nano-patterned features having a non-random topography. The method also includes fabricating a two-dimensional (2D) micro-grid array including a plurality of sensors. The method further includes coupling the comb structure to the 2D micro-grid array.

Embodiments of the present invention are directed to a method of using a neural three-dimensional (3D) comb sensor structure. A non-limiting example of the method includes inserting the neural 3D comb sensor structure into grey and white matter of a brain of an individual. The neural 3D sensor comb sensor structure includes a first comb and a second comb, each including a plurality of shanks including nano-patterned features having a non-random topography. The method further includes monitoring electrical activity of the individual's brain function.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
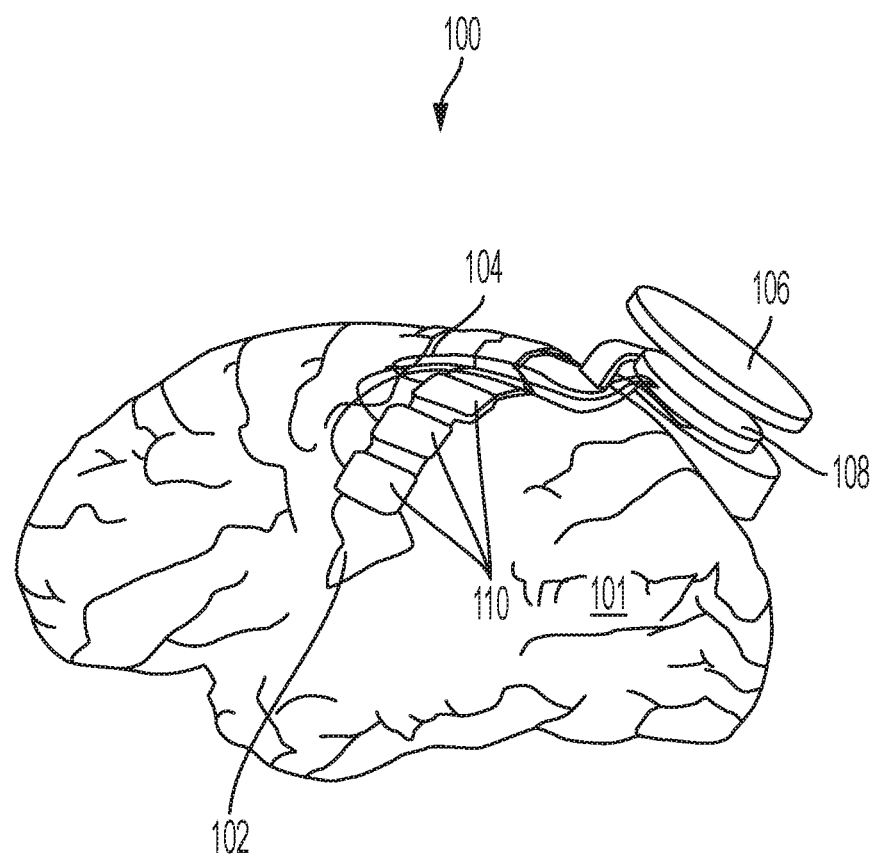
FIG. 1 depicts a schematic diagram of a system for brain monitoring and stimulation featuring an array of 3D comb probe sensor units implanted into the cerebral cortex of an individual's brain according to embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

For the sake of brevity, conventional techniques related to semiconductor fabrication may or may not be described in detail herein. Moreover, the various tasks and process steps described herein can be incorporated into a more comprehensive procedure or process having additional steps or functionality not described in detail herein. In particular, various steps in the manufacture of semiconductors are well-known and so, in the interest of brevity, many conventional steps will only be mentioned briefly herein or will be omitted entirely without providing the process details known to those skilled in art.

Turning now to an overview of technologies that are more specifically relevant to aspects of the invention, while recent improvements in neural probes have reduced the electrode size, commercially available electrodes are cumbersome in size and feature only a small number of electrode contacts per device, e.g., less than 20 electrode contacts. While useful for bulk stimulations and limited electrical sensing, commercially available devices also do not include a high enough density of electrodes to be useful in quantifying and understanding the behavior of individual cells. Moreover, the use of surface-based electrode grids only interact with and measure electrical signals from the top surface of the brain, as the electrodes only contact this surface. Therefore, it is not possible to accurately measure the electrical properties a 3D region of the brain.

Turning now to an overview of the aspects of the invention, one or more embodiments of the invention address the above-described shortcomings of the prior art by providing an implantable neural device for any part of the cortical surface, including the somatosensory cortex. The implantable system for brain monitoring and stimulation includes a modular structure with 3D comb sensor units connected to a hub arranged within the skull cavity by flexible biocompatible interconnects. The hub receives wireless power from an external wearable unit and can distribute power to multiple 3D comb sensor units, as well as receive and process data for neuron read/write activity and manages bidirectional wireless telemetry between the external wearable unit and the multiple 3D comb sensor units. Each 3D comb sensor unit includes unitary comb structures with multiple shanks per comb structure for deep cortical recording, and a 2D micro-grid array that rests on the brain surface for sensing and recording electrical signals from superficial neuron populations and providing electrical stimulation as needed. The 3D comb sensor units and 2D micro-grid arrays include nano-topography, e.g., nanorods, all of which are fabricated using semiconductor manufacturing techniques known to those in the art.

The above-described aspects of the invention address the shortcomings of the prior art by using nano-topography on the electrode surfaces to provide both high-resolution electrical sensing plus 3D sensing and analysis based on a 3D comb sensor structure. The nano-topography on the exposed surfaces of the sensing elements significantly increases the surface area of the sensing elements, and therefore, the electrical signal and sensitivity of the electrodes. The depths in which the individual shanks which include the comb arrays are inserted and the spacings of the shanks within the comb arrays are specifically designed to minimize any injury to the brain cortex and abate the potential for neurological side effects.

Figure 2:
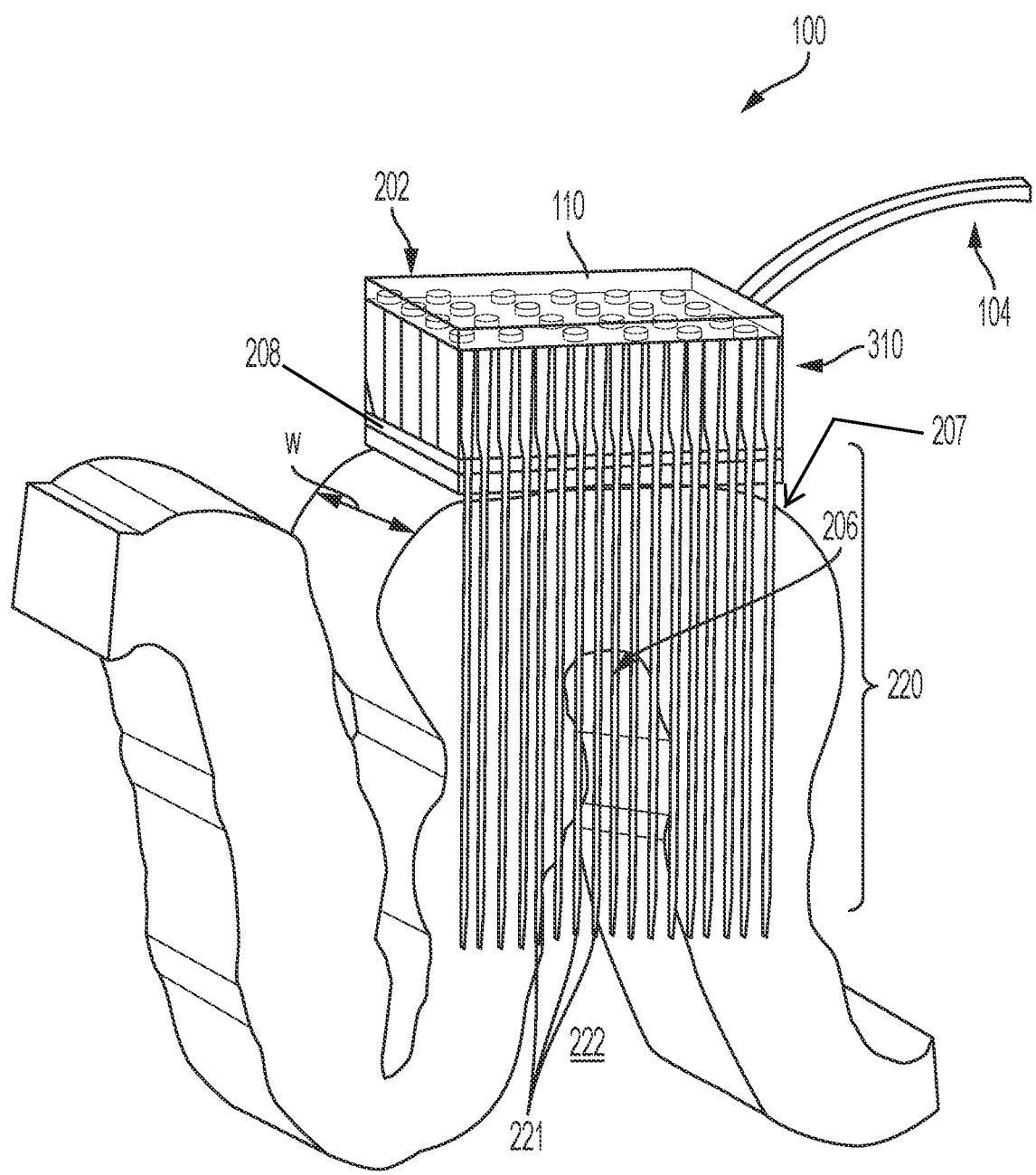
FIG. 2 depicts a schematic diagram of a 3D comb probe sensor unit arranged on a neural fold according to embodiments of the present invention.

Turning now to a more detailed description of aspects of the present invention, FIG. 1 depicts a schematic diagram of a system for brain monitoring and stimulation 100 implanted into the neural cortex of a brain 101 of an individual according to embodiments of the present invention. The system for brain monitoring and stimulation 100 includes a plurality of 3D comb sensor devices 110 (also referred to as sensor modules). Each 3D comb sensor device 110 includes a plurality of unitary comb structures 220 including individual shanks 221 (as shown in FIG. 2) that are inserted into the primary somatosensory cortex 102 of the brain 101. Although three 3D comb sensor devices 110 are depicted in FIG. 1, the system for brain monitoring and stimulation 100 can include any number of 3D comb sensor devices 110, for example, one, two, three, or four, or more comb sensor devices 110.

The 3D comb sensor device 110 are coupled to an internal hub 108 (also referred to as an internal skull hub) by flexible interconnects 104 (also referred to herein as biocompatible interconnects) that include a biocompatible material. The internal hub 108 is arranged in the skull cavity is coupled to and receives wireless power from an external wearable power supply 106 (also referred to as an external skull power supply). In some embodiments of the present invention, power supply 106 is a battery-operated device, and power supply 106 also transfers power to internal hub 108 without a direct wired electrical connection. The internal hub 108 provides power and a two-way data stream to the plurality of 3D comb sensor devices 110 through the plurality of flexible interconnects, which prevent damage from unwanted module and device movement in the brain 101.

The exposed outer surfaces of flexible interconnects 104 that interact with the outer surfaces of brain 101 include a flexible biocompatible material. In one or more embodiments of the present invention, exposed outer surfaces of the flexible interconnects 104 include a polymeric material. According to one or more embodiments of the present invention, the flexible polymeric material includes a polyimide material. In other embodiments of the present invention, the flexible polymeric material includes one or more materials from polymer families such as silicone, polyethylene, polyvinyl chloride, polyurethane, or polylactides. According to some embodiments of the present invention, the biocompatible material traditionally encases an electrically conductive wiring material, such as copper.

FIG. 2 depicts a schematic diagram of the 3D comb sensor device 110 arranged on a neural fold according to embodiments of the present invention. A gyrus 207 is the ridge on the cerebral cortex, which is adjacent to one or more sulcus 206 (depressions or furrows). The 3D comb sensor devices 110 are placed across the gyms 207 width (w), rather than lengthwise, such that each of the combs 220 extend over each side gyms 207. Each 3D comb sensor device 110 includes at least one comb structure 220 (see FIG. 3A) with a plurality of shanks 221. In one or more embodiments of the present invention, the 3D comb sensor device 110 includes two combs 220. Yet, in some embodiments of the present invention, each 3D comb sensor device 110 includes more than two combs, for example, four combs, which can be arranged around the perimeter of 2D microgrid array 208.

The lengths of the shanks 221 in each comb 220 are inserted into the cortex and extend into the white matter 222, so that the combs 220 completely traverse the layers of the cortex and are tethered in the white matter 222 (the superficial aspect of the gyms 207 being the grey matter). The shanks 221 can interact with the neurons throughout the various layers of cortex and axons within the white matter 222. The length of the shanks are sufficient to provide sensors across the entire depth of the cortex and mechanically probe into the white matter 222 to anchor the comb device 100 while minimizing tissue damage. The lengths of the shanks 221 in the combs 220 therefore permit sampling of the cortex buried in the sulcus 206 at either end of the comb 220, which provides for dense sampling across the gyms 207, while still protecting normal neural tissue between the combs 220. The combs 220 have a flexible construction that allows them to adapt to brain micro and macro movement with respirations and vascular pulsations.

The length (L) of each shank 221 is ideally sufficient in length to fully sample the entire plurality of layers of grey matter and penetrate into white matter. The shanks 221 should anchor the white matter to provide mechanical support, as well as provide one or more electrical reference signals. The white matter contains largely axons, and the dearth of neurons in this region provides an electrically quiet region to use as a reference. A reference electrode (not shown) can be included at the end shanks 221 in order to sample the reference signal from the white matter. The signal from the reference electrode can be used to discern if the placement of the 3D comb sensor devices 110 successfully penetrate the white matter. According to one or more embodiments of the present invention, the length (L) (see FIG. 3A) of the shanks 221 in each 3D comb is about 8 to about 12 mm. According to exemplary embodiments of the present invention, the length (L) of the shanks 221 is about 10 mm. Yet, according to other embodiments of the present invention, the length (L) of the shanks 221 is about 12 to about 24 mm.

Figure 3B:
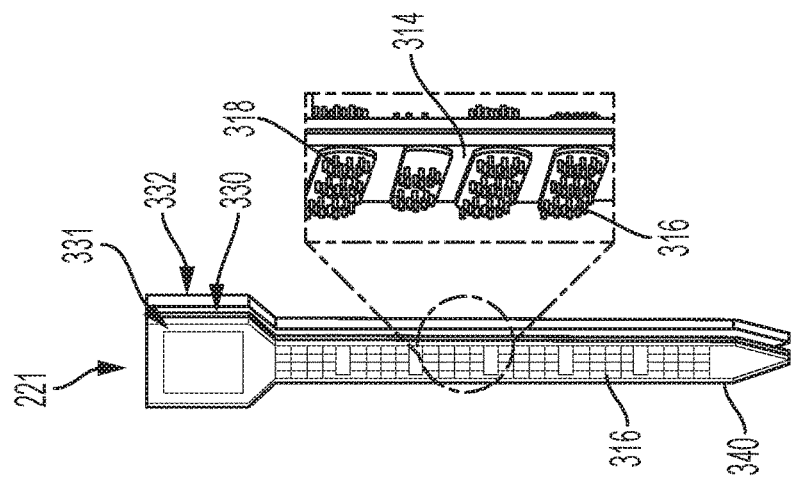
FIG. 3B depicts a schematic diagram showing an expanded view of a shank of the comb probe of FIG. 3A.
Figure 3A:
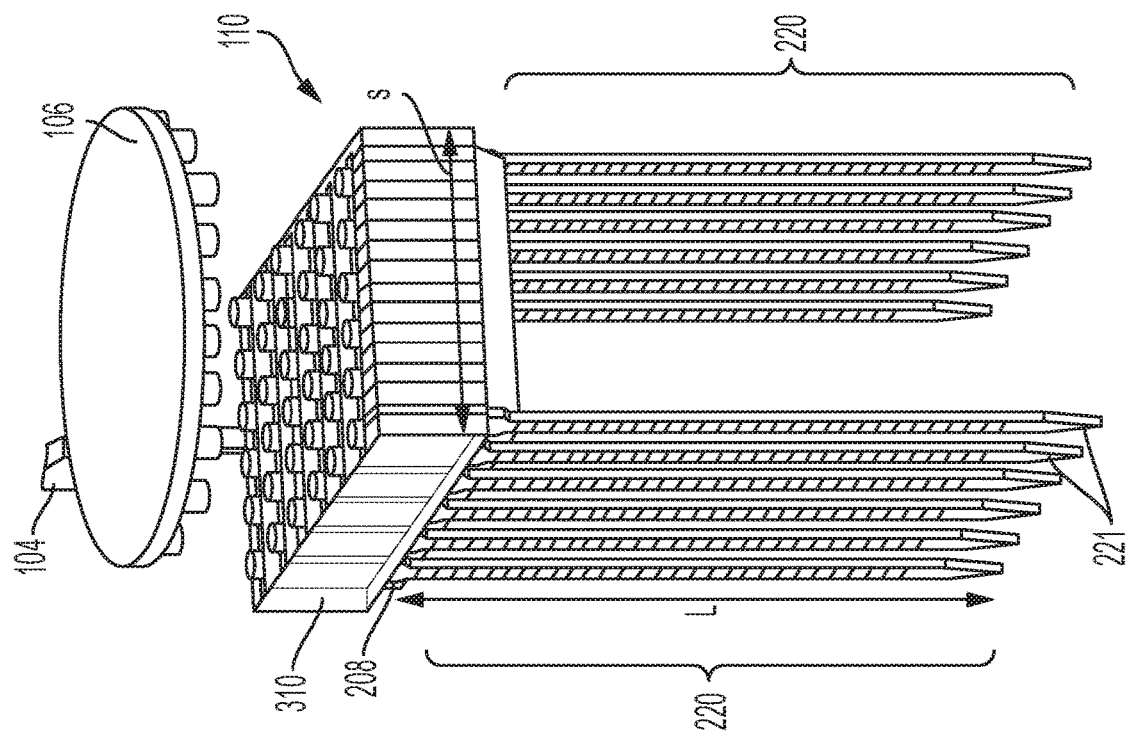
FIG. 3A depicts a schematic diagram of a comb probe according to embodiments of the present invention.

Each 3D comb sensor device 110 of the system for brain monitoring and stimulation 100 also includes a control chip 202 (see FIG. 2), a 2D micro-grid array 208 (see FIG. 3A), and an interposer support structure 310 (see also FIG. 3A). The 3D combs 220 each include a plurality of shanks 221, each having a shank base that is inserted into the interposer support structure 310. The 2D micro-grid array 208 is mounted on the bottom surface of the 3D comb sensor device 110 and includes a plurality of sensor contacts arranged in a 2D array that rest on the brain (gyms 207) for recording from superficial neuron populations. According to one or more embodiments of the present invention, the 2D micro-grid array 208 includes about 50,000 to about 150,000 read electrode sensing elements 316, and about 5,000 to about 15,000 write electrode sensing elements 316 (see also FIG. 3A). The 2D micro-grid array 208 further includes recording, stimulating, and interfacing circuitry. The 3D comb sensor device control chip 202, or a logic chip, controls power distribution and data interface between the hub 108 and the 2D micro-grid array 208/3D combs 220.

FIG. 3A depicts a schematic diagram of the 3D comb sensor device 110 according to embodiments of the present invention. FIG. 3B depicts a schematic diagram showing an expanded view of a shank 221 of the 3D comb sensor device 110 shown in FIG. 3A.

Each comb sensor device 110 includes one, two, or more combs 220. Combs 220 can be three-dimensional in that a comb structure can feature sensing elements on both the exposed surfaces of shanks 221 which are oriented in both the direction towards the control chip 202 as well as in the direction away from control chip 202. Although two 3D combs 220 are shown, embodiments of the present invention are not limited to two combs. The spacing (s) between the combs 220 is designed to minimize brain tissue damage and enables successful 3D sensing. According to one or more embodiments of the present invention, the spacing (s) between the combs 220 is about 3 mm to about 6 mm. According to exemplary embodiments of the present invention, the spacing (s) between the combs 220 is about 5 mm. Yet, according to some embodiments of the present invention, the spacing (s) between the combs 220 is about 4 to about 5 mm.

According to one or more embodiments of the present invention, each comb 220 includes about 32 to about 36 shanks 221. According to exemplary embodiments of the present invention, each comb 220 includes about 34 shanks 221. Yet, according to other embodiments of the present invention, each comb 220 includes about 20 to about 50 shanks 221.

In one or more embodiments of the present invention, shank 221 is double sided with sensing elements 316 arranged on a first side 331 (front side) and the second side 332 (back side). In other embodiments of the present invention, shank 221 can feature sensing elements arranged on only one side of a shank. In the case of a double sided shank 221 structure, the first side 331 and the second side 332 of each shank 221 includes a substrate 402 (see FIG. 4A) onto which a plurality of sensing elements 316 are formed. The substrate 402 can be a semiconductor substrate, a polymeric material, or a biocompatible material. The sensing elements 316 on first side 331 and second side 332 are separated by spacing 314 (see FIG. 3B) in order to insure that sensing elements 316 are articulated as individual sensors. Spacing 314 includes a dielectric material. The first side 331 and the second side 332 are joined together, with the non-patterned faces of first side 331 and second side 332 aligned face-to-face, leaving the faces of shank 221 with sensing elements exposed to and encompassed by brain 101. The joining method for the first side 331 and the second side 332 of shank 221 can include a bonding layer 330, or in another embodiment the faces of sides 331 and 332 may also be joined directly utilizing direct treatment of the exposed surfaces. The bonding layer 330 can include an adhesive, a ceramic-ceramic bond, or a metal-metal bond. The adhesive 330 includes, according to exemplary embodiments of the present invention, a polyimide adhesive.

The sensing elements 316 on the first side 331 contact the brain interstitial tissue when implanted and provide sensing and stimulation of the surrounding neurons. The sensing elements 316 on the second side 332 actively control the collection of the reading from and drive stimulating desired neurons as well.

The dimensions of sensing elements 316 are designed to ideally sense and provide stimulation to a minimal amount of neurons per sensing elements. The geometry of the sensing elements 316 are not restricted by the scope of the invention; the sensing elements can feature a square shape, a hexagonal shape, or other 2D geometry. In one or more embodiments of the present invention, the critical dimension of the sensing elements 316 range from 5 μm to 50 μm. In other embodiments of the present invention, the critical dimension can range from 5 μm to 20 μm. In yet some embodiments of the present invention, sensing elements 316 can be square in geometry with a critical dimension of 10 um. According to one or more embodiments of the present invention, the first side 331 and the second side 332 each include about 375 to about 88,000 sensing elements 316, dependent on the sensing element critical dimension, shank length, and shank width as previously described herein.

The sensing elements 316 can be arranged in any manner on the first side 331 and the second side 332. For example, the sensing elements 316 may be arranged in a grid structure optimized for density. Additionally, the sensing elements 316 can be arranged in alternating layers of 2 and 3 sensors, as shown in FIG. 3B. Yet, the arrangement is not limited to this orientation.

The large number of strategically arranged sensing elements 316 on each shank 221 and on the 3D comb sensor device 110 provides very rich spatial coverage for sensing and stimulation. Given this rich coverage, it is possible that when a single neuron fires then that action potential will be recorded at more than one sensing element 316. The multiple recordings of the same action potential are able to acquire a richer description of the action potential by combining the recordings, triangulating where the neuron lay in space, and using this information to be able to electrically stimulate a single neuron by using a pattern of stimulation signals such that the resultant charge targeted the single neuron. The large number of sensing elements 316 provides more sensors than signal paths. Therefore, different sensors 316 can be sub-selected as needed for sensing and stimulation of precisely targeted areas of brain 101.

The 3D comb sensor device 110 is designed to reduce injury by becoming part of the gyral topography, or a system integrated into the brain. The design overcomes one of the most significant obstacles with existing arrays of densely packed 3D probes, which is injury produced at the sites of implantation. Such injury results in a neuro-inflammatory response, which is perpetuated by micro-motion of the stiff electrodes within the cortex. To reduce injury to the brain, the shanks 221 are constructed to be of appropriate stiffness to provide for smooth pial and brain penetration and remain flexible, so that they can move with the respiratory and vascular motion in the brain.

As also depicted in FIG. 3B, each sensing element 316 on the surfaces of the shanks 221 includes nano-patterned features 318 which provides two benefits to 3D comb sensor device 110. Nanopatterned features 318 reduce the tissue injury response after insertion and promote interaction of neurons with the sensing element 316 surfaces. Using appropriately sized nano-patterned features 318 reduce microglial activation and antibody responses. The nano-patterned features 318 also enhance neural signal quality during sensing due to the increased surface area of sensing elements 316. Additionally, the nanopatterned features enable more stimulation of more targeted portions of brain 101.

According to one or more embodiments of the present invention, the shanks 221, plus the sensing elements 316 and/or the associated nanopatterned features 318, also include a coating 420 that includes a biocompatible and biodegradable material. The coating on the shanks 221 renders them stiff enough for insertion, but degrades after insertion over the course of several hours, leaving a more flexible construct.

According to one or more embodiments of the present invention, the coating 420 includes polyethylene glycol (PEG). According to other embodiments of the present invention, the coating includes a PEG hydrogel supplemented with poly-D-lysine. Other non-limiting examples of coatings 340 include fast degrading polycarbonate, bioresorbable saccharose, extracellular matrix proteins, or any combination thereof. The suitability of the type of coating 340 used will depend on the length of individual electrodes and the spacing (pitch) between them.

Figure 4A:
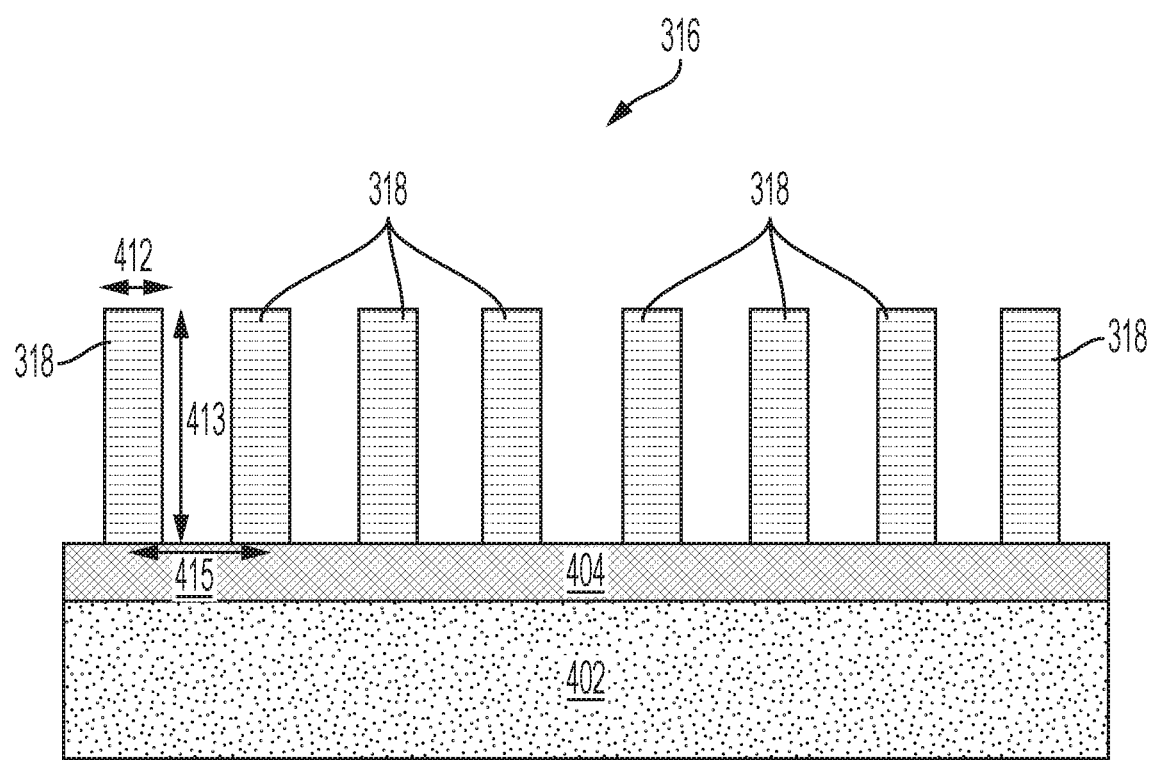
FIG. 4A depicts a cross-sectional side view of a sensing element with nano-features according to embodiments of the present invention.

FIG. 4A depicts a cross-sectional side view of a sensing element 316 with nanopatterned features 318 according to embodiments of the present invention. Each sensing element 316 is formed on a substrate 402 that includes a semiconductor material. A base layer 404 is formed on the substrate 402, and nanopatterned features 318 are formed on the base layer 404. In one or more embodiments of the present invention, base layer 404 functions as an electrode.

The term "semiconductor material" denotes a material that has an electrical conductivity value between a conductor, such as copper, and an insulator, such as glass. Semiconductor materials can be elemental materials or compound materials. Examples of semiconductor materials that can be used as substrate include Si, SiGe, SiGeC, SiC, Ge alloys, MN compound semiconductors or II/VI compound semiconductors. The substrate 402 can also include a dielectric material.

The base layer 404 arranged on the substrate 402 includes one or more conductive materials. Since sensing elements 316 are designed to be in direct contact with portions of brain 101, a biocompatible material is needed for base layer 404. The conductive material can include a metallic material, including an alloy of more than one metal. The conductive material can include an alloy of metallic components, or metallic and non-metallic components. The conductive material can include, but is not limited to, platinum, copper, silver, gold, tungsten, aluminum, iron, palladium, nickel, titanium, zirconium, phosphorus, carbon, or a combination thereof. In one or more embodiments of the present invention, the conductive material is in a crystalline state. In other embodiments of the present invention, the conductive material is in an amorphous state.

The base layer 404 incorporated in sensing elements 316 and the nanopatterned features 318 can be formed by traditional semiconductor fabrication methods known in the art. Depending on the material selected for base layer 404, various semiconductor processing methods can be used to fabricate the electrode surfaces on the shanks 221. According to exemplary embodiments of the present invention, a damascene process incorporating utilizing photolithography to form the base electrode shape in a dielectric layer in-plane, followed by filling the patterned base layer shape electroplated metal (e.g., platinum or gold) can be used. In embodiments where a metallic material is utilized to form base layer 404, additional methods such as PVD or ALD may be used to form base layer 404.

Located on the exposed surface of base layer 404, the nano-patterned features 318 form a non-random topography on a surface of the base layer 404. The nano-patterned features 318 are an array of non-random (i.e., regular repeating) repeating individually articulated features formed on the base layer 404. The repeating individually articulated features can have various shapes and sizes. Non-limiting examples of shapes for each repeating individually articulated features include rods, cones, annular structures (e.g., hollow tubes), or any combination thereof.

In one or more embodiments of the present invention, the nano-patterned features 318 have a critical dimension 412, i.e., diameter or width, from about 5 nm to about 600 nm. In other embodiments of the present invention, the nano-patterned features 318 have a critical dimension from about 20 nm to about 300 nm. In some embodiments of the present invention, the nano-patterned features 318 have a height 413 from about 5 nm to about 20 micrometers (μm). In one or more embodiments of the present invention, each of nanopatterned features 318 has an aspect ratio (i.e., ratio of width to height) of from about 1:1 to about 50:1. In other embodiments of the present invention, each of nano-patterned features 318 has a pitch 415 of from about 2:1 to 20:1. "Pitch" 415 refers to the center-to-center distance of nearest-neighbor features.

The nano-patterned features 318 include one or more conductive material(s). The conductive material forming the nano-patterned features 318 can be the same as the conductive material forming the base layer 404 according to some embodiments of the present invention. Yet, in other embodiments of the present invention, the conductive material forming the nano-patterned features 318 is different than the conductive material forming the base layer 404. The conductive material forming the nano-patterned features 318 can include a metallic material, including an alloy of more than one metal. The conductive material can include an alloy of metallic components, or an alloy of metallic and non-metallic components. The conductive material can include, but is not limited to, platinum, copper, silver, gold, tungsten, aluminum, iron, palladium, nickel, titanium, zirconium, phosphorus, carbon, or a combination thereof. In one or more embodiments of the present invention, the conductive material is in a crystalline state. In other embodiments of the present invention, the conductive material is in an amorphous state.

Depending on the materials used for the nano-patterned features 318, various methods can be used to form the nano-patterned features 318. According to some embodiments of the present invention, the nano-patterned features 318 are formed using direct electroplating. Yet, in other embodiments of the present invention, the material forming the nano-patterned features 318 can be overgrown and subsequently etched back to the desired size/shape/dimension. Photolithography, etching, and chemical mechanical planarization (referred to as CMP), are other non-limiting examples of methods that can be used to form the nano-patterned features 318 on the surface of the base layer 404.

Figure 4B:
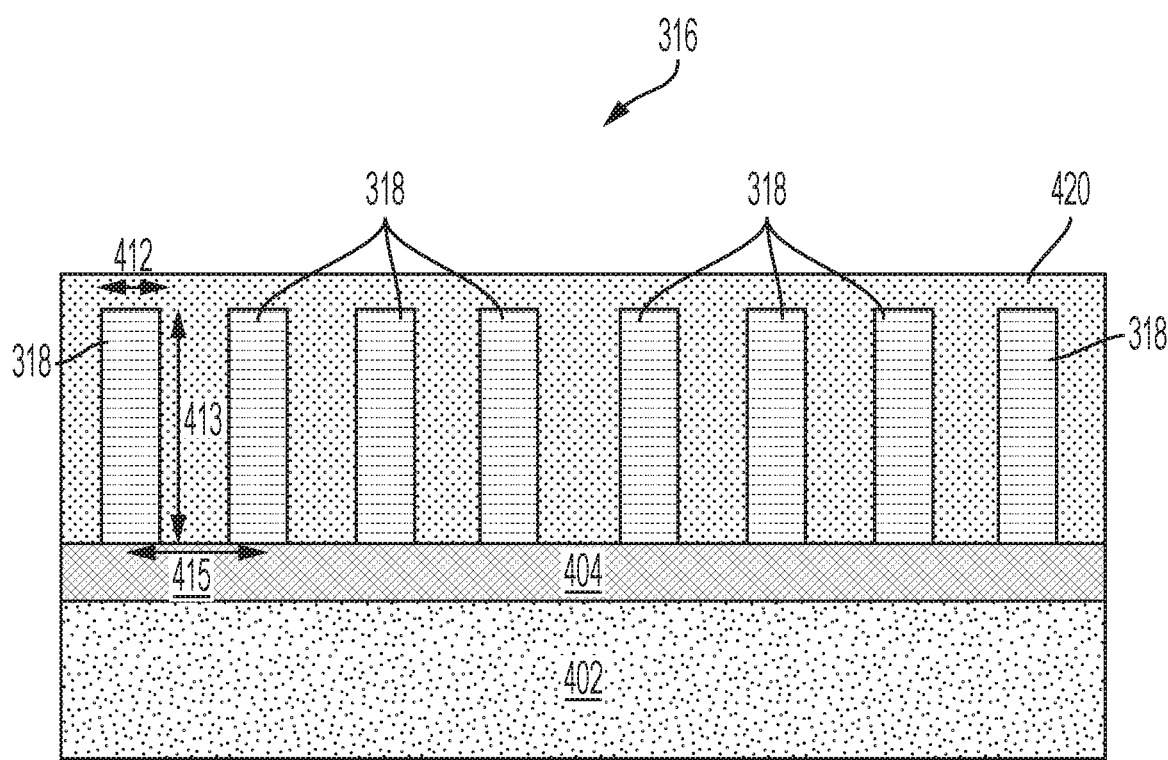
FIG. 4B depicts a cross-sectional side view of a dissolveable biocompatible layer encasing the exposed surfaces of the sensing element features according to embodiments of the present invention.

Referring to FIG. 4B, according to one or more embodiments of the present invention, the shanks 221 include a temporary coating 420 which is biocompatible and biodegradable. The coating on the shanks 221 renders them stiff enough for insertion, but degrades after insertion over the course of several hours, leaving a more flexible construct.

Sensing elements 316, including nanopatterned features 318 as well as base layer 404, can also be covered by temporary coating 420. In one or more embodiments of the present invention, temporary coating 420 encapsulates the exposed surfaces of both sensing elements 316 and nanopatterned features 318, as illustrated in FIG. 4B. In yet other embodiments of the present invention, temporary coating 420 is in contact with top surface and/or partial portions of the sidewall of nanopatterned features 318, while base layer 404 is not in direct contact with temporary coating 420 (not shown).

According to one or more embodiments of the present invention, the temporary coating 420 includes polyethylene glycol (PEG). According to other embodiments of the present invention, the coating includes a PEG hydrogel supplemented with poly-D-lysine. Other non-limiting examples of coatings 420 include fast degrading polycarbonate, bioresorbable saccharose, extracellular matrix proteins. The suitability of the type of temporary coating 420 used will depend on the length of individual electrodes and the spacing (pitch) between them.

According to one or more embodiments of the present invention, a method of using the system for brain monitoring and stimulation 100 includes inserting the neural 3D comb sensor device structure 110 into both grey and white matter of an individual's brain. The neural 3D comb sensor device structure 110 includes a first comb and a second comb each including a plurality of shanks 221 featuring sensing elements 316 which include nano-patterned features 318 having a non-random topography.

According to other embodiments of the present invention, a method of using the system for brain monitoring and stimulation 100 includes implanting the 3D comb sensor unit 110 in the somatosensory cortex. The system for brain monitoring and stimulation 100 is coupled to an external prothesis, for example an artificial limb. Sensors are placed in the outer surface or "skin" and within the prosthesis to measure external signals, which are conveyed as input to the sensory cortex to provide sensation from the artificial skin of the prosthetic and positional and other environmental information of the prosthetic.

According to some embodiments of the present invention, a method of using the system for brain monitoring and stimulation 100 includes implanting the 3D comb sensor unit 110 in cortex. The system for brain monitoring and stimulation is coupled to an external prosthesis or device. The external prosthesis or device provides visual, auditory, temperature, or other sensory signals as input to different parts of the brain.

According to one or more additional embodiments of the present invention, a method of using the system for brain monitoring and stimulation 100 includes implanting the 3D comb sensor device 110 in the somatosensory cortex. The system for brain monitoring and stimulation 100 is coupled to an external prosthesis. The 3D comb sensor device 110 monitors neuronal activity in the motor cortex and conveys the information to an external robotic arm or limb to activate the robotic arm or limb. In addition, the 3D comb device 110 includes stimulation capabilities that can provide feedback information regarding the position or motion of the external robotic device.

According to some embodiments of the present invention, the 3D comb sensor device 110 can be used to block or contain a seizure in a patient with epilepsy, preventing the seizure from spreading down a gyms through selective stimulation of different electrode contacts. Given the dimensions of the 3D structure, its placement on a gyms and the large number of sensors it is possible to monitor and modulate or stimulate individual neurons to restrict a seizure within a certain volume of the gyms and stop its spread out of that volume. Bracketting the seizure at the onset area in this manner would conceivably stop the seizure from propagating and keep it within a very small volume and limit its deleterious effects.

According to other embodiments of the present invention, the 3D comb sensor device 110 can be used to replace the Utah array in other cortical regions for single neuron sampling. The 3D comb sensor device 110 can be used to provide feedback for memory consolidation.

While the systems described herein are described for brain monitoring and stimulation, the systems are not limited to these applications and can be used in a variety of other physiological applications, including but not limited to, biological and environmental applications. Electrical sensing and stimulation may be useful for interaction with other areas impacted by the nervous system, such as the spinal cord. Even for devices which do not directly produce electrical signals, enzyme or other bioactive agents may be applied to the surface of the probe to produce indirect electrical signal by electrochemical reactions. Additionally, 3D comb sensor device 101 may be implantable on external skin surface, as well as other organs which may benefit from electrical stimulation. Broader environmental applications may also benefit from 3D spatial measurements from 3D comb sensor device 101.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The phrase "selective to," such as, for example, "a first element selective to a second element," means that the first element can be etched and the second element can act as an etch stop.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

As previously noted herein, for the sake of brevity, conventional techniques related to semiconductor device and integrated circuit (IC) fabrication may or may not be described in detail herein. By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combination of the operations described in connection with the fabrication of a semiconductor device according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), and chemical-mechanical planarization (CMP), and the like. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device. Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A structure for monitoring and stimulation comprising:
   an external power supply unit;
   an internal hub communicatively coupled to the external power supply unit; and
   a plurality of sensor modules communicatively coupled to the internal hub by a plurality of flexible interconnects, each of the plurality of sensor modules comprising:
   an interposer support structure;
   a two-dimensional (2D) micro-grid array on a bottom surface of the interposer; and
   a three-dimensional (3D) comb sensor device comprising only two combs, a first comb and a second comb separated by about 2 to about 6 millimeters (mm), wherein the first comb and the second comb each include a plurality of shanks, each shank comprising a shank base inserted into the interposer support structure, wherein the first comb and the second comb are arranged to extend from the bottom surface of the interposer and along opposite sidewalls of an outermost perimeter of the 2D micro-grid array, wherein an end of each shank comprises a reference electrode to sample a reference signal from white matter after anchoring the end of each respective shank into the white matter;
   wherein each shank of the plurality of shanks comprises a double-sided shank having thereon a first plurality of sensing elements on a first side and a second plurality of sensing elements on a second side opposite the first side, each sensing element comprising a plurality of nano-patterned features protruding from an island, the sensing elements separated by dielectric spacers such that each respective sensing element is articulated as an individual sensor, wherein a first island comprises a first number of nano-patterned features and a second island comprises a second number of nano-patterned features different than the first number of nano-patterned features.

2. The structure of claim 1, wherein the nano-patterned features comprise non-random topography comprising repeating individually articulated features, each repeating individually articulated feature comprising rods, cones, or annular structures.

3. The structure of claim 2, wherein the each repeating individually articulated feature has an aspect ratio from about 1:1 to about 50:1, and a pitch from about 2:1 to about 20:1.

4. The structure of claim 1, wherein surfaces of the 3D comb sensor devices are encased by a temporary coating.

5. The structure of claim 1, wherein the plurality of flexible interconnects comprises a polyimide material.

6. A three-dimensional (3D) comb sensor structure comprising:
   a plurality of sensor modules, the 3D comb sensor structure comprising:
   an interposer support structure;
   a two-dimensional (2D) micro-grid array on a bottom surface of the interposer, the 2D micro-grid array comprising a plurality of first sensing elements;
   only two combs, a first comb and a second comb, each communicatively coupled to the 2D micro-grid array and comprising second sensing elements, the first comb and the second comb separated by about 2 to about 6 millimeters (mm), wherein the first comb and the second comb each include a plurality of shanks, each shank comprising a shank base inserted into the interposer support structure, wherein the first comb and the second comb are arranged to extend from the bottom surface of the interposer and along opposite sidewalls of an outermost perimeter of the 2D micro-grid array, wherein an end of each shank comprises a reference electrode to sample a reference signal from white matter after anchoring the end of each respective shank into the white matter; and a logic chip coupled to the 2D micro-grid array that controls power distribution and data interface between the 2D micro-grid array and each of the first comb and the second comb;

wherein each shank of the plurality of shanks comprises a double-sided shank having thereon a first plurality of the second sensing elements on a first side and a second plurality of the second sensing elements on a second side opposite the first side, each sensing element comprising a plurality of nano-patterned features protruding from an island, the sensing elements separated by dielectric spacers such that each respective sensing element is articulated as an individual sensor, wherein a first island comprises a first number of nano-patterned features and a second island comprises a second number of nano-patterned features different than the first number of nano-patterned features.

7. The structure of claim 6, wherein the nano-patterned features comprise non-random topography comprising repeating individually articulated features, each repeating individually articulated feature comprising rods, cones, or annular structures.

8. The structure of claim 7, wherein the each repeating individually articulated feature has an aspect ratio from about 1:1 to about 50:1, and a pitch from about 2:1 to about 20:1.

9. The structure of claim 6, wherein each of the first comb and the second comb features sensing elements on both exposed surfaces.

10. The structure of claim 6, wherein the nano-patterned features further comprise a temporary coating arranged thereon.

11. A three-dimensional (3D) comb sensor structure comprising:

an interposer support structure;

a two-dimensional (2D) micro-grid array on a bottom surface of the interposer; and a first comb and a second comb, each of the first comb and the second comb comprising a plurality of linearly arranged shanks, each shank comprising a shank base inserted into the interposer support structure, each of the first comb and the second comb are arranged to extend from the bottom surface of the interposer and along opposite sidewalls of an outermost perimeter of the 2D micro-grid array and comprising sensing elements containing a plurality of nanorods, wherein an end of each shank comprises a reference electrode to sample a reference signal from white matter after anchoring the end of each respective shank into the white matter; and a logic chip coupled to the 2D micro-grid array that controls power distribution and data interface between the 2D micro-grid array and each of the first comb and the second comb, the first comb and the second comb separated by about 2 to about 6 millimeters (mm), and the first comb and the second comb being immediately adjacent to one another;

wherein each shank of the plurality of shanks comprises a double-sided shank having thereon a first plurality of the sensing elements on a first side and a second plurality of the sensing elements on a second side opposite the first side, each sensing element comprising the plurality of nanorods protruding from an island, the sensing elements separated by dielectric spacers such that each respective sensing element is articulated as an individual sensor, wherein a first island comprises a first number of nano-patterned features and a second island comprises a second number of nano-patterned features different than the first number of nano-patterned features.

12. The structure of claim 11, wherein each nanorod of the plurality of nanorods has an aspect ratio from about 1:1 to about 50:1, and a pitch from about 2:1 to about 20:1.

13. The structure of claim 11, wherein each of the shanks of the first comb and the second comb has a length of about 8 to about 12 millimeters (mm).

14. The structure of claim 13, wherein surfaces of the 3D comb sensor structure are encompassed by a temporary coating.

* * * * *